United States Patent
Weber et al.

(10) Patent No.: US 8,221,743 B2
(45) Date of Patent: Jul. 17, 2012

(54) USE OF POLYPEPTIDES AGAINST DISEASES CAUSED BY PROTOZOANS

(75) Inventors: Gilbert Weber, Magden (CH); Jiri Broz, Rheinfelden (CH)

(73) Assignee: Novozymes A/S, Bagsvaerd (DK)

( * ) Notice: Subject to any disclaimer, the term of this patent is extended or adjusted under 35 U.S.C. 154(b) by 149 days.

(21) Appl. No.: 12/520,230

(22) PCT Filed: Dec. 13, 2007

(86) PCT No.: PCT/EP2007/011058
§ 371 (c)(1),
(2), (4) Date: Jul. 10, 2009

(87) PCT Pub. No.: WO2008/077521
PCT Pub. Date: Jul. 3, 2008

(65) Prior Publication Data
US 2010/0021446 A1 Jan. 28, 2010

(30) Foreign Application Priority Data

Dec. 22, 2006 (EP) .................................. 06026710
Feb. 5, 2007 (EP) .................................. 07002444

(51) Int. Cl.
*A01N 63/00* (2006.01)
*A01N 37/18* (2006.01)
(52) U.S. Cl. ...................................... 424/93.46; 514/4.4
(58) Field of Classification Search .................. 514/4.4; 424/93.46
See application file for complete search history.

(56) References Cited

U.S. PATENT DOCUMENTS 7,883,711 B2 * 2/2011 Gormsen et al. ........... 424/246.1

FOREIGN PATENT DOCUMENTS

| | | |
|---|---|---|
| EP | 0561907 | 9/1998 |
| RU | 2 219 238 | 12/2003 |
| WO | WO 96/16177 | 5/1996 |
| WO | WO 96/17929 | 6/1996 |
| WO | WO 98/30682 | 7/1998 |
| WO | WO 98/35026 | 8/1998 |
| WO | WO 99/00489 | 1/1999 |
| WO | WO 00/22103 | 4/2000 |
| WO | WO 00/26230 | 5/2000 |
| WO | WO 00/26354 | 5/2000 |
| WO | WO 01/83559 | 11/2001 |
| WO | WO 03/009700 | 2/2003 |
| WO | WO 2006/099871 | 9/2006 |

OTHER PUBLICATIONS

Animal Health Care Center 2002; Canine Coccidiosis, www.animalhealthcare.com/handouts/general/coccidiosis.htm.*
Kritas et al., J. Vet. Med., Series A, vol. 53, pp. 170-173 (2006).
Lebbadi et al., Arch. Microbiol., vol. 162, pp. 98-102 (1994).
Cordovilla et al., J. Euk. Mibrobiol, vol. 40, No. 3, pp. 323-328 (1993).

* cited by examiner

*Primary Examiner* — Karen Carlson
(74) *Attorney, Agent, or Firm* — Elias Lambiris

(57) ABSTRACT

The present invention relates to the use of isolated polypeptides as coccidiostats and/or histomonastats. An example of a polypeptide of the invention is the so-called L12 protein from *Bacillus licheniformis* ATCC 14580.

18 Claims, No Drawings

SEQUENCE LISTING

```
<160> NUMBER OF SEQ ID NOS: 10

<210> SEQ ID NO 1
<211> LENGTH: 381
<212> TYPE: DNA
<213> ORGANISM: Bacillus licheniformis
<220> FEATURE:
<221> NAME/KEY: CDS
<222> LOCATION: (1)..(378)
<220> FEATURE:
<221> NAME/KEY: mat_peptide
<222> LOCATION: (124)..(378)

<400> SEQUENCE: 1 atg aaa aat cat ttg tat gag aaa aaa aag agg aaa cct ttg act cgg      48
Met Lys Asn His Leu Tyr Glu Lys Lys Lys Arg Lys Pro Leu Thr Arg
    -40                 -35                 -30 aca att aaa gcg acg ctc gcc gtg ttg aca atg tcc atc gct ttg gtg      96
```

```
Thr Ile Lys Ala Thr Leu Ala Val Leu Thr Met Ser Ile Ala Leu Val
-25             -20                 -15                 -10 gga ggc gct acg gtg cct tca ttt gca tgg gtg aat ccg ggt tat cac      144
Gly Gly Ala Thr Val Pro Ser Phe Ala Trp Val Asn Pro Gly Tyr His
            -5              -1  1               5 tac cag tac cca tcg gaa ggt ggt aca tgg agg tat gga ttc gta aac      192
Tyr Gln Tyr Pro Ser Glu Gly Gly Thr Trp Arg Tyr Gly Phe Val Asn
            10              15                  20 gcc ggg ctc cgt tca gag tac aac cac ccg aca aag gtc cac ggc tcg      240
Ala Gly Leu Arg Ser Glu Tyr Asn His Pro Thr Lys Val His Gly Ser
        25              30              35 aca gtg caa aag ctc atc gat gga aaa gtg gat aaa acg aat aga agt      288
Thr Val Gln Lys Leu Ile Asp Gly Lys Val Asp Lys Thr Asn Arg Ser
40          45              50              55 att gat acg gct gcg ggc cgc tac tct aat gcc tat gtc gga gcc ata      336
Ile Asp Thr Ala Ala Gly Arg Tyr Ser Asn Ala Tyr Val Gly Ala Ile
                60              65              70 aac tca cct ggt ctt aag ggt cgt tac tac tat cgc acc aac taa          381
Asn Ser Pro Gly Leu Lys Gly Arg Tyr Tyr Tyr Arg Thr Asn
            75              80              85

<210> SEQ ID NO 2
<211> LENGTH: 126
<212> TYPE: PRT
<213> ORGANISM: Bacillus licheniformis

<400> SEQUENCE: 2

Met Lys Asn His Leu Tyr Glu Lys Lys Arg Lys Pro Leu Thr Arg
    -40             -35                 -30

Thr Ile Lys Ala Thr Leu Ala Val Leu Thr Met Ser Ile Ala Leu Val
-25             -20                 -15                 -10

Gly Gly Ala Thr Val Pro Ser Phe Ala Trp Val Asn Pro Gly Tyr His
            -5              -1  1               5

Tyr Gln Tyr Pro Ser Glu Gly Gly Thr Trp Arg Tyr Gly Phe Val Asn
            10              15                  20

Ala Gly Leu Arg Ser Glu Tyr Asn His Pro Thr Lys Val His Gly Ser
        25              30              35

Thr Val Gln Lys Leu Ile Asp Gly Lys Val Asp Lys Thr Asn Arg Ser
40          45              50              55

Ile Asp Thr Ala Ala Gly Arg Tyr Ser Asn Ala Tyr Val Gly Ala Ile
                60              65              70

Asn Ser Pro Gly Leu Lys Gly Arg Tyr Tyr Tyr Arg Thr Asn
            75              80              85

<210> SEQ ID NO 3
<211> LENGTH: 1581
<212> TYPE: DNA
<213> ORGANISM: Bacillus licheniformis
<220> FEATURE:
<221> NAME/KEY: CDS
<222> LOCATION: (601)..(978)

<400> SEQUENCE: 3
gaattttccg gaagctgaaa cacccgtgat atatataacc ataaattaaa cagcataggc     60
ggattgtgcg agttcctcca cattcggagt atttctgaat gatagagcca cacggtccac    120
gttctcactg gctaaccgga tcaaatgatc ttcaggagtc agcataatac atccagttca    180
ggtagataag atttgaattt ggtgacttgc ttttgttctt cttctttcat tttctgacta    240
atccaaactg gaaaaagcag gtcttttaac agattaggag gtttctgaca tgcaccattc    300
```

```
ggtcactaac cgaatgcagt aaaggacact gtggtgcttg ccagccatta gggtattgag      360
gaggtgatca aaatgctagg tgacagtatt tcgtcgaagt ggacaagtcg tgaccaaatg      420
acctcggatc gagggttggt catggaggaa aaaattgatg tctggtgaca agaggagtc       480 atgatcatgg caccgccaac gagggaaaaa actcttcccg catcgacacg tatgtgggc       540 ggtgacaaac taacttatag agtaaattta ttagtcgaat gaaagaggag gaatgaaata      600
```

```
atg aaa aat cat ttg tat gag aaa aaa aag agg aaa cct ttg act cgg       648
Met Lys Asn His Leu Tyr Glu Lys Lys Lys Arg Lys Pro Leu Thr Arg
1                5                  10                 15 aca att aaa gcg acg ctc gcc gtg ttg aca atg tcc atc gct ttg gtg       696
Thr Ile Lys Ala Thr Leu Ala Val Leu Thr Met Ser Ile Ala Leu Val
            20                  25                  30 gga ggc gct acg gtg cct tca ttt gca tgg gtg aat ccg ggt tat cac       744
Gly Gly Ala Thr Val Pro Ser Phe Ala Trp Val Asn Pro Gly Tyr His
        35                  40                  45 tac cag tac cca tcg gaa ggt ggt aca tgg agg tat gga ttc gta aac       792
Tyr Gln Tyr Pro Ser Glu Gly Gly Thr Trp Arg Tyr Gly Phe Val Asn
    50                  55                  60 gcc ggg ctc cgt tca gag tac aac cac ccg aca aag gtc cac ggc tcg       840
Ala Gly Leu Arg Ser Glu Tyr Asn His Pro Thr Lys Val His Gly Ser
65                  70                  75                  80 aca gtg caa aag ctc atc gat gga aaa gtg gat aaa acg aat aga agt       888
Thr Val Gln Lys Leu Ile Asp Gly Lys Val Asp Lys Thr Asn Arg Ser
                85                  90                  95 att gat acg gct gcg ggc cgc tac tct aat gcc tat gtc gga gcc ata       936
Ile Asp Thr Ala Ala Gly Arg Tyr Ser Asn Ala Tyr Val Gly Ala Ile
            100                 105                 110 aac tca cct ggt ctt aag ggt cgt tac tac tat cgc acc aac                978
Asn Ser Pro Gly Leu Lys Gly Arg Tyr Tyr Tyr Arg Thr Asn
        115                 120                 125
```

```
taatcaaagg gaaaacggtt gctgtcaacg gggctagcat ggcaagaccc agaaaagttc     1038
tgggagatcc cgctttgcat aagcgtatta tagtggatga cgcgggcttt gttgtttaca     1098
cttcttgcac ctgctgacgg caatcatccc tatctatgaa atcgagattt cagcaggccg     1158
ttattttcga gagagttaaa tctatattca ttgttttat tttggtaagg acataccgga      1218
ttttaggttt ggattaccgg tcgagttagc ttgtcttttc gcccactacc gtgtcgatgc     1278
gggagcaatt taccagaagc acttaccgat tgatagtttt ttattccggt gattgcaaag    1338
tttcataaac tctgagaatt caatagggg aataccccgc tttgaggggc gcggcatttt     1398 atgcgcccg agtatttatt cttaaaattt taaattaat gtatctatat aaaaaggaga      1458
tgctttcggt gtactgccaa agcatctcca caaagatag tgcatatctg caggaaaaa      1518 cataaaatgc aactaacatt ttttggaaa gcaataggtt tatttaattt tgtagttta      1578 tct                                                                   1581
```

<210> SEQ ID NO 4
<211> LENGTH: 126
<212> TYPE: PRT
<213> ORGANISM: Bacillus licheniformis

<400> SEQUENCE: 4

```
Met Lys Asn His Leu Tyr Glu Lys Lys Lys Arg Lys Pro Leu Thr Arg
1                5                  10                 15

Thr Ile Lys Ala Thr Leu Ala Val Leu Thr Met Ser Ile Ala Leu Val
            20                  25                  30

Gly Gly Ala Thr Val Pro Ser Phe Ala Trp Val Asn Pro Gly Tyr His
        35                  40                  45
```

```
Tyr Gln Tyr Pro Ser Glu Gly Gly Thr Trp Arg Tyr Gly Phe Val Asn
    50                  55                  60
Ala Gly Leu Arg Ser Glu Tyr Asn His Pro Thr Lys Val His Gly Ser
65                  70                  75                  80
Thr Val Gln Lys Leu Ile Asp Gly Lys Val Asp Lys Thr Asn Arg Ser
                85                  90                  95
Ile Asp Thr Ala Ala Gly Arg Tyr Ser Asn Ala Tyr Val Gly Ala Ile
                100                 105                 110
Asn Ser Pro Gly Leu Lys Gly Arg Tyr Tyr Tyr Arg Thr Asn
            115                 120                 125

<210> SEQ ID NO 5
<211> LENGTH: 15
<212> TYPE: PRT
<213> ORGANISM: Bacillus licheniformis
<220> FEATURE:
<221> NAME/KEY: MISC_FEATURE
<223> OTHER INFORMATION: N-terminal

<400> SEQUENCE: 5

Trp Val Asn Pro Gly Tyr His Tyr Gln Tyr Pro Ser Glu Gly Gly
1               5                   10                  15

<210> SEQ ID NO 6
<211> LENGTH: 31
<212> TYPE: DNA
<213> ORGANISM: Artificial Sequence
<220> FEATURE:
<223> OTHER INFORMATION: Primer Pep 481
<220> FEATURE:
<221> NAME/KEY: misc_feature
<223> OTHER INFORMATION: Primer

<400> SEQUENCE: 6
aattacgcgt gttggtgcga tagtagtaac g                              31

<210> SEQ ID NO 7
<211> LENGTH: 29
<212> TYPE: DNA
<213> ORGANISM: Artificial Sequence
<220> FEATURE:
<223> OTHER INFORMATION: Primer Pep 482
<220> FEATURE:
<221> NAME/KEY: misc_feature
<223> OTHER INFORMATION: Primer

<400> SEQUENCE: 7
ttaagaattc gaatgaaaga ggaggaatg                                 29

<210> SEQ ID NO 8
<211> LENGTH: 125
<212> TYPE: PRT
<213> ORGANISM: Bacillus licheniformis
<220> FEATURE:
<221> NAME/KEY: mat_peptide
<222> LOCATION: (41)..(125)

<400> SEQUENCE: 8

Met Lys Asn Leu Leu Asn Lys Lys Arg Lys Pro Leu Thr Arg Thr
-40                 -35                 -30                 -25
Ile Lys Ala Thr Phe Ala Val Leu Thr Val Ser Ile Gly Leu Val Gly
                -20                 -15                 -10
Gly Ala Thr Val Pro Ala Phe Ala Trp Val Asn Pro Asp Tyr His Tyr
            -5                  -1  1                   5
```

-continued

```
Gln Tyr Pro Ser Glu Gly Gly Thr Trp Arg Tyr Gly Phe Val Asn Leu
         10                  15                  20

Gly Leu Arg Ser Glu Tyr Asn His Pro Lys Lys Val His Gly Ser Thr
 25                  30                  35                  40

Val Gln Lys Leu Ile Asp Gly Lys Val Glu Lys Thr Asn Arg Ser Leu
                 45                  50                  55

Asp Thr Ala Pro Gly Arg Tyr Ser Asn Ala Tyr Val Gly Val Val Asn
             60                  65                  70

Ser Pro Gly Leu Lys Gly Arg Tyr Tyr Tyr Arg Thr Asn
         75                  80                  85

<210> SEQ ID NO 9
<211> LENGTH: 126
<212> TYPE: PRT
<213> ORGANISM: Bacillus licheniformis
<220> FEATURE:
<221> NAME/KEY: mat_peptide
<222> LOCATION: (42)..(126)

<400> SEQUENCE: 9

Met Lys Asn Tyr Leu Tyr Glu Lys Lys Arg Lys Pro Leu Thr Arg
    -40                 -35                 -30

Thr Ile Lys Ala Thr Leu Ala Val Leu Thr Met Ser Ile Ala Leu Val
-25                 -20                 -15                 -10

Gly Gly Ala Thr Val Pro Ala Phe Ala Trp Val Asn Pro Gly Tyr His
             -5                  -1   1               5

Tyr Gln Tyr Pro Ser Glu Gly Gly Thr Trp Arg Tyr Gly Phe Val Asn
         10                  15                  20

Ala Gly Leu Arg Ser Glu Tyr Asn His Pro Thr Lys Val His Gly Ser
 25                  30                  35

Thr Val Gln Lys Leu Ile Asp Gly Lys Val Asp Lys Thr Asn Arg Ser
 40                  45                  50                  55

Ile Asp Thr Ala Ala Gly Arg Tyr Ser Asn Ala Tyr Val Gly Ala Ile
             60                  65                  70

Asn Ser Pro Gly Leu Lys Gly Arg Tyr Tyr Tyr Arg Thr Asn
         75                  80                  85

<210> SEQ ID NO 10
<211> LENGTH: 126
<212> TYPE: PRT
<213> ORGANISM: Artificial Sequence
<220> FEATURE:
<223> OTHER INFORMATION: Consensus sequence
<220> FEATURE:
<221> NAME/KEY: mat_peptide
<222> LOCATION: (42)..(126)

<400> SEQUENCE: 10

Met Lys Asn His Leu Tyr Glu Lys Lys Arg Lys Pro Leu Thr Arg
    -40                 -35                 -30

Thr Ile Lys Ala Thr Leu Ala Val Leu Thr Met Ser Ile Ala Leu Val
-25                 -20                 -15                 -10

Gly Gly Ala Thr Val Pro Ala Phe Ala Trp Val Asn Pro Gly Tyr His
             -5                  -1   1               5

Tyr Gln Tyr Pro Ser Glu Gly Gly Thr Trp Arg Tyr Gly Phe Val Asn
         10                  15                  20

Ala Gly Leu Arg Ser Glu Tyr Asn His Pro Lys Val His Gly Ser
 25                  30                  35

Thr Val Gln Lys Leu Ile Asp Gly Lys Val Asp Lys Thr Asn Arg Ser
 40                  45                  50                  55
```

```
Ile Asp Thr Ala Ala Gly Arg Tyr Ser Asn Ala Tyr Val Gly Ala Ile
            60                  65                  70

Asn Ser Pro Gly Leu Lys Gly Arg Tyr Tyr Tyr Arg Thr Asn
            75                  80              85
```

USE OF POLYPEPTIDES AGAINST DISEASES CAUSED BY PROTOZOANS

CROSS-REFERENCE TO RELATED APPLICATIONS

This application is a 35 U.S.C. 371 national application of PCT/EP2007/011058 filed Dec. 17, 2007, which claims priority or the benefit under 35 U.S.C. 119 of European application nos. EP 06026710.1 and EP 07002444.3 filed Dec. 22, 2006 and Feb. 5, 2007, respectively, the contents of which are fully incorporated herein by reference.

The present invention relates to the use of polypeptides related to a *Bacillus licheniformis* polypeptide (amino acids 1-85 of SEQ ID NO: 2) for the treatment and the prophylaxis of diseases caused by protozoans, for example as coccidiostat and/or histomonastat in pharmaceutical applications, including veterinary applications. An example of a polypeptide of the invention is the so-called L12 protein from *Bacillus licheniformis* ATCC 14580, which has the amino acid sequence of amino acids +1 to +85 of SEQ ID NO:2 herein (in what follows amino acids 1-85 of SEQ ID NO:2).

Coccidia is a generic name given to single cell protozoan organisms that are intestinal parasites that infect both vertebrates and invertebrates. The organisms cause coccidiosis, and usually settle in the small intestine, such as the colon. Infections of animals, e.g. farm animals, with coccidia can not only seriously reduce growth, but it can be lifethreatening. Symptoms from coccidial infection include loss of epithelial cells, the denuding of gut mucosa, and diarrhea (often with a concomitant loss of blood). For some farm animals, such as poultry, coccidial infection can be fatal, if not seriously damaging to the animal's health.

Poultry are particularly vulnerable for coccidiosis because of several reasons: (1) The parasitic cycle of 6 to 8 days hits them at a critical stage between weeks 2 and week 4, when maximum growth is usually expressed. Since the parasites virtually destroy the whole intestinal epithelium, the absorption of nutrients is dramatically reduced, which results in marked growth depression. Until slaughter at 5 or 6 weeks, there is not enough time to recover. (2) There are 7 species of *Eimeria* which can infect poultry, more than in any other animal category, and at least 4 of them are regularly seen in commercial operations. Thus, when one infectious cycle is concluded already another one can be at an early stage so that coccidiosis becomes chronic. (3) In poultry the most pathogenic species (*Eimeria tenella, E. necatrix*) are observed, which induce severe hemorrhages and in certain cases can cause a mortality of up to 50%. Such an acute case of coccidiosis could easily ruin a poultry farmer. (4) The intensive husbandry of poultry (100,000 chicks or more in one house) on deep litter facilitates access of poultry to the infectious stages of coccidia in the faeces via coprophagy and thus supports a fast spreading of the disease through a whole poultry flock. If the sanitary conditions are not rigorous, the disease will also transfer to other poultry houses on the same farm and stay on site for years.

Histomonaisis is also caused by a protozoan. In this specific case the protozoa infects the ceca, and later the liver, of turkeys, chickens, and occasionally other galliform birds. In turkeys, most infections are fatal; in other birds, mortality is less common. The protozoan parasite *Histomonas meleagridis* is transmitted most often in embryonated eggs of the cecal nematode *Heterakis gallinarum*, and sometimes directly by contact with infected birds. Outbreaks spread quickly through flocks by direct contact. A large percentage of chickens harbor this worm, and histomonads have been located in adult worms of both sexes. Three species of earthworms can harbor *H gallinarum* larvae containing *H meleagridis*, which are infective to both chickens and turkeys. *H meleagridis* survives for long periods within *Heterakis* eggs, which are resistant and may remain viable in the soil for years. Histomonads are released from *Heterakis* larvae in the ceca a few days after entry of the nematode and replicate rapidly in cecal tissues. The parasites migrate into the submucosa and muscularis mucosae and cause extensive and severe necrosis. Histomonads reach the liver either by the vascular system or via the peritoneal cavity, and rounded necrotic lesions quickly appear on the liver surface. Histomonads interact with other gut organisms, such as bacteria and coccidia, and depend on these for full virulence.

Traditionally, histomonaisis has been thought of as affecting turkeys, while doing little damage to chickens. However, outbreaks in chickens may cause high morbidity, moderate mortality, and extensive culling. Liver lesions tend to be less severe in chickens, but morbidity can be especially high in young layer or breeder pullets.

The term animal includes all animals. Examples of animals are non-ruminants, and ruminants. Ruminant animals include, for example, animals such as sheep, goat, and cattle, e.g. cow such as beef cattle and dairy cows. In a particular embodiment, the animal is a non-ruminant animal. Non-ruminant animals include pet animals, e.g. dogs or cats and mono-gastric animals, e.g. pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn).

The present invention is based on the finding that polypeptides hereinafter defined have activity against diseases caused by protozoans, preferably against coccidiosis and histomonaisis and therefore can be used for example as coccidiostat and/or histomonastat in pharmaceutical applications. Although said polypeptides have already been suggested as additives for animal feed (WO-A-2006/099871), it has not been realized, until now, that these compounds could have been active against coccidia. Indeed, in WO-A-2006/099871, the polypeptides were instead added to animal feed in order to improve animal feed utilization by improving the feed conversion ratio (FCR), and/or modulating the gut microflora, and there was no mention of any activity against coccidiosis or histomonaisis.

Therefore, in a first aspect, this invention relates to the use of a polypeptide selected from the group consisting of:
(a) a polypeptide comprising an amino acid sequence which has a degree of identity to amino acids 1-85 of SEQ ID NO:2 of at least 33%;
(b) a polypeptide which is encoded by a nucleic acid sequence which hybridizes under low stringency conditions with (i) nucleotides 124-378 of SEQ ID NO: 1, (ii) a subsequence of (i) of at least 100 nucleotides, or (iii) a complementary strand of (i), or (ii);
(c) a variant of the polypeptide having an amino acid sequence of amino acids 1-85 of SEQ ID NO:2 comprising a substitution, deletion, extension, and/or insertion of one or more amino acids;
(d) an allelic variant of (a) or (b); and
(e) a fragment of (a), (b), (c), or (d).
in the manufacture of a pharmaceutical composition for the treatment or prophylaxis of diseases caused by protozoans, preferably for the treatment or prophylaxis of coccidiosis and/or histomonaisis.

By using a polypeptide as defined above as a coccidiostat for example, one can employ a naturally occurring compound which is more likely to be acceptable to the human or animal being treated for coccidiosis. Also, industry and consumer groups are often in favor of using naturally occurring compounds rather than synthetic ones. The polypeptides are organic, and may therefore be cheaper to provide than synthetic inorganic compounds.

In a second aspect, the present invention relates to a method of treatment, or prophylaxis of coccidiosis and/or histomonaisis in the human or animal body, the method comprising administering polypeptides according to the invention to that human or animal.

The polypeptides of the invention may be used (i) in therapy, i.e. for treatment of coccidiosis and/or histomonaisis, and/or (ii) for prophylaxis, i.e. treatment to prevent the onset of coccidiosis and/or histomonaisis ("primary" prophylaxis), and/or the recurrence of symptoms in an existing infection that has been brought under control ("secondary" prophylaxis, maintenance therapy).

The polypeptides of the invention may be used (a) in veterinary medicine, which is the application of medical, diagnostic, and therapeutic principles to companion, domestic, exotic, wildlife, and production animals; and/or (b) in human medicine.

In a third aspect, the invention relates to pharmaceutical including veterinary compositions comprising the polypeptide of the invention. In a particular embodiment, the present invention relates to a pharmaceutical composition comprising a polypeptide of the invention and a suitable carrier.

Isolated nucleic acid sequences encoding the polypeptides as defined hereinabove, nucleic acid constructs, vectors and host cells comprising the nucleic acid sequences for expressing and production of isolated polypeptides as hereinabove defined as well as polypeptide compositions for further use and preparation according to this invention and strains as exemplified hereinafter are described in WO-A-2006/099871. The content of this publication, in particular variants of polypeptides and strains according to the inventions and their production, is hereby incorporated by reference.

In particular embodiments the polypeptide has, consists essentially of, or consists of an amino acid sequence which has a degree of identity to amino acids 1-85 of SEQ ID NO:2 of at least 33%, such as, e.g., the polypeptide of amino acids 1-85 of SEQ ID NO:2. Other specific examples are the polypeptides of amino acids 1-85 of any one of SEQ ID NOs:8, 9, and 10 (identified as L12-likes on the basis of the PCR-test of Example 1 herein).

A polypeptide of the present invention may be a bacterial or a fungal polypeptide. In a second particular embodiment, the polypeptide is a Gram positive bacterial polypeptide such as a Bacillus polypeptide or a variant thereof, for example a Bacillus licheniformis polypeptide e.g. derived from Bacillus licheniformis ATCC 14580, which is the type strain of Bacillus licheniformis and available on request from the American Type Culture Collection, ATCC. Preferred strains of Bacillus licheniformis are positive in the test of Example 1 herein, such as the following strains of Bacillus licheniformis: ATCC 14580 (=NCIB 9375), NCIMB 6346 (=DSM 8785), NCTC 1024, NCTC 1025, NCTC 2120, NCTC 7589, NCTC 9932, ATCC 21424, NCIMB 10689, and ATCC 53757.

According to the invention the polypeptide can be used as isolated pure polypeptide or in a mixture of polypeptides.

As defined herein, an "isolated" or "pure" polypeptide is a polypeptide which is essentially free of other polypeptides, e.g., at least 80% pure, preferably at least 85%, 86%, 87%, 88%, 89%, or at least 90% pure, more preferably at least 91%, 92%, 93%, 94%, 95%, or at least 96% pure, as determined by SDS-PAGE (e.g., by coomassie-staining and subsequent scanning by methods known in the art). Purity may also be determined by HPLC, preferably RP-HPLC (e.g., using a Waters μ-Bondapak C18 column, Mobil phase A: 0.1% TFA, Mobil phase B: Acetonitrile+0.1% TFA, detecting at 280 nm). The SDS-PAGE purity, as well as the HPLC purity, refers to the amount of the polypeptide of the invention, relative to the amount of total protein. In alternative embodiments, the polypeptide may be at least 20%, 40%, 60%, or at least 70% pure.

The amount of total protein can be determined by any method known in the art, e.g. the Kjeldahl method (A.O.A.C., 1984, Official Methods of Analysis 14th ed., Association of Official Analytical Chemists, Washington D.C.), and the amount of the polypeptide of the invention can be determined by SDS-PAGE and subsequent scanning, also by methods known in the art.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

In a specific embodiment, the polypeptide is a low-allergenic variant, designed to invoke a reduced immunological response when exposed to animals, including man. The term immunological response is to be understood as any reaction by the immune system of an animal exposed to the polypeptide. One type of immunological response is an allergic response leading to increased levels of IgE in the exposed animal. Low-allergenic variants may be prepared using techniques known in the art. For example the polypeptide may be conjugated with polymer moieties shielding portions or epitopes of the polypeptide involved in an immunological response. Conjugation with polymers may involve in vitro chemical coupling of polymer to the polypeptide, e.g. as described in WO 96/17929, WO98/30682, WO98/35026, and/or WO99/00489. Conjugation may in addition or alternatively thereto involve in vivo coupling of polymers to the polypeptide. Such conjugation may be achieved by genetic engineering of the nucleotide sequence encoding the polypeptide. Another way of providing low-allergenic variants is genetic engineering of the nucleotide sequence encoding the polypeptide so as to cause the polypeptides to self-oligomerize, effecting that polypeptide monomers may shield the epitopes of other polypeptide monomers and thereby lowering the antigenicity of the oligomers. Such products and their preparation is described e.g. in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the polypeptide by known gene manipulation techniques such as site directed mutagenesis (see e.g. WO 00/26230, WO 00/26354 and/or WO 00/22103) and/or conjugation of a polymer may be done in sufficient proximity to the epitope for the polymer to shield the epitope.

The pharmaceutical compositions may be prepared in accordance with methods known in the art and may be in the form of a liquid or a dry composition. The polypeptide to be included in the composition may be stabilized in accordance with methods known in the art.

The dosage of the polypeptide composition of the invention and other conditions under which the composition is used may be determined on the basis of methods known in the art.

Generally, the composition of the invention comprises an effective amount of the antimicrobial polypeptide of the invention. The term "effective amount" when used herein is intended to mean an amount of the polypeptides of the invention, which is sufficient to inhibit growth of the microorganism in question.

Formulations of the polypeptides of the invention may be administered to a host suffering from or predisposed to a coccidiosis infection. Generally the dose of the polypeptides of the invention will be sufficient to decrease the microbial population by at least about 50%. The polypeptides (or compounds) of the present invention may be administered at a dosage that reduces the microbial population while minimizing any side-effects. It is contemplated that the composition will be obtained and used under the guidance of a physician or veterinarian for in vivo use.

Various methods for administration may be employed. The pharmaceutical formulation may be given orally, or may be injected intravascularly, subcutaneously, peritoneally, by aerosol, opthalmically, intra-bladder, topically, etc. The dosage of the therapeutic formulation will vary widely, depending on the frequency of administration, the manner of administration and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously. The amide bonds, as well as the amino and carboxy termini, may be modified for greater stability on oral administration. For example, the carboxy terminus may be amidated.

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, creams, foams, solutions, suppositories and injections. As such, administration of the compounds can be achieved in various ways, including oral, buccal, rectal, parenteral, intraperitoneal, intradermal, transdermal, intracheal, etc., administration. The polypeptides of the invention may be localized by the use of an implant or other formulation that acts to retain the active dose at the site of implantation.

For oral preparations, the compounds may be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds may be formulated into preparations for injections by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Furthermore, the compounds may be made into suppositories by mixing with a variety of bases such as emulsifying bases or water-soluble bases. The compounds of the present invention may be administered rectally via a suppository. The suppository may include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing the antimicrobial polypeptides of the invention is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The composition may further comprise another pharmaceutically active agent, such as an additional biocidal agent, such as another antimicrobial polypeptide exhibiting antimicrobial activity as defined above or such as another coccidiostats.

The biocidal agent may be an antibiotic, as known in the art. Classes of antibiotics include penicillins, e.g. penicillin G, penicillin V, methicillin, oxacillin, carbenicillin, nafcillin, ampicillin, etc.; penicillins in combination with beta-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. The biocidal agent may also be an anti-mycotic agent, including polyenes, e.g. amphotericin B, nystatin; 5-flucosyn; and azoles, e.g. miconazol, ketoconazol, itraconazol and fluconazol.

Anti-mycotic agents may also be useful, including polyenes, e.g. amphotericin B, nystatin; 5-flucosyn; and azoles, e.g. miconazol, ketoconazol, itraconazol and fluconazol. Antituberculotic drugs include isoniazid, ethambutol, streptomycin and rifampin. Cytokines may also be included in a formulation of the antimicrobial polypeptides of the invention, e.g. interferon gamma, tumor necrosis factor alpha, interleukin 12, etc.

Examples of other coccidiostats which may also be used are ionophores such as lasalocid, monensin, salinomycin, maduramycin, semduramycin and chemical agents as amprolium, nicarbazin, diclazuril.

As disclosed in WO-A-2003/009700 polyunsaturated fatty acids have been discovered to have coccidiostatic activity as well. Therefore, in a particular preferred embodiment of the invention further active ingredients of the pharmaceutical composition are polyunsaturated fatty acids (PUFAs).

The PUFA can either be a single PUFA or two or more different PUFAs. Each PUFA can be of the n-3 or n-6 family. Preferably it is a C18, C20 or C22 PUFA. It may have at least 18 carbon atoms and 3 double bonds. The PUFA can be provided in the form of a free fatty acid, a salt, as a fatty acid ester (e.g. methyl or ethyl ester), as a phospholipids and/or in the form of a mono-, di- or triglyceride.

Suitable (n-3 and n-6) PUFAs include:
docosahexaenoic acid (DHA, 22: 6$\Omega$3), suitably from algae or fungi, such as the (dinoflagellate) *Crypthecodinium* or the (fungus) *Thraustochytrium;*
y-linolenic acid (GLA, 18: $\Omega$6);
a-linolenic acid (ALA, 18: $\Omega$3);
conjugated linoleic acid (octadecadienoic acid, CLA);
dihomo-y-linolenic acid (DGLA, 20: $\Omega$6);
arachidonic acid (ARA, 20: $\Omega$6); and
eicosapentaenoic acid (EPA, 20: 5 $\Omega$3).

Preferred PUFAs include arachidonic acid (ARA), docosohexaenoic acid (DHA), eicosapentaenoic acid (EPA) and/or y-linoleic acid (GLA). In particular, ARA is preferred.

The PUFA may be from a natural (e.g. vegetable or marine) source or may be derived from a single cell or microbial source. In particular, the PUFA may be produced by a bacteria, alga, fungus or yeast. Fungi are preferred, preferably of the order Mucorales, for example *Mortierella, Phycomyces, Blakeslea, Aspergillus, Thraustochytrium, Pythium* or *Entomophthora*. The preferred source of ARA is from *Mortierella alpina, Blakeslea trispora, Aspergillus terreus* or *Pythium insidiosum*. Algae can be dinoflagellate and/or include *Porphyridium, Nitszchia,* or *Crypthecodinium* (e.g. *Crypthecodinium cohnii*).

Yeasts include those of the genus *Pichia* or *Saccharomyces*, such as *Pichia ciferii*. Bacteria can be of the genus *Propionibacterium*.

The PUFA may be present in or be added to the composition as an (e.g. edible) oil. The oil may be a liquid (at room temperature). The oil may be a microbial (e.g. single cell), marine (e.g. tuna) oil or a vegetable oil. A suitable oil that includes ARA is available from DSM N. V., Alexander Fleminglaan 1 or Wateringseweg 1, P.O. Box 1,2600 MA Delft, The Netherlands, under the trade mark VEVODAR. Another commercially available (ARA) oil is ARASCO from Martek Corporation, 6480 Dobbin Road, Columbia, Md. 21045, United States of America. Other PUFAs are available, for example DHA as a DHA oil (DHASCO from Martek Corporation or DHA from Pronova, Norway, under the trademark PAX).

A number of documents describe the production of crude PUFA oils. Microbial oils containing ARA are disclosed in WO-A-92/13086 (Martek), EPA in WO-A-91/14427 (Martek) and DHA in WO-A-91/11918 (Martek). Various methods for extracting PUFA oils from microbial sources can be found in WO-A-97/36996 and WO-A-97/37032 (both Gist-brocades). Preparation of ARA, DHA and EPA-containing oils is also described in WO-A-92/12711 (Martek).

It is preferred that most of the PUFA is in the form of triglycerides. Thus, preferably at least 50%, such as at least 60%, or optimally at least 70%, of the PUFA is in triglyceride form. However, the amount of triglycerides may be higher, such as at least 85%, preferably at least 90%, optimally at least 95% or 98% of the oil.

In a fourth aspect, the invention relates to the pharmaceutical use, as well as all other uses referred to above, of a strain of *Bacillus* which is positive in the test of Example 1 herein.

Accordingly, each and every particular embodiment of the first, second, and third aspect of the present invention are specifically applicable also to this aspect of the invention, and specifically included herein, e.g.:

I. Use of a *Bacillus* strain which is positive in the test of Example 1 herein in the preparation of a pharmaceutical formulation, e.g. medicament, for the treatment of coccidiosis.

II. A method of medical treatment comprising administering a *Bacillus* strain which is positive in the test of Example 1 herein to an individual in need of medical treatment against coccidiosis.

III. A pharmaceutical composition comprising a *Bacillus* strain which is positive in the test of Example 1 herein and a suitable carrier for use as a coccidiostat.

The expression "a strain of *Bacillus* which is positive in the test of Example 1 herein" means that the DNA of the *Bacillus* strain, when harvested and used as a DNA template in a PCR reaction with SEQ ID NOs:4 and 5 as primers, leads to the generation of a PCR fragment of a size of approximately 0.4 kb. This test serves to identify strains with a L12-like gene.

In a particular embodiment, the *Bacillus* strain is used in the form of spores. Spores may be exospores or, preferably, endospores. An endospore is any spore that is produced within an organism (usually a bacterium).

In another particular embodiment, the PCR fragment, when purified and sequenced encodes an amino acid sequence which has at least 33% identity to amino acids 1-85 of SEQ ID NO:2. In further particular embodiments the PCR fragment, when purified and sequenced, encodes an amino acid sequence which has a degree of identity to amino acids 1-85 of SEQ ID NO:2 of at least 35%, or a least 37%, 40%, 42%, 45%, 47%, 50%, 52%, 55%, 57%, 60%, 62%, 65%, 67%, 70%, 72%, 75%, 77%, 80%, 82%, 85%, 87%, 90%, 92%, 95%, 97%, or at least 99%.

In further particular embodiments, the strain of *Bacillus* is a strain of *Bacillus licheniformis*, preferably selected from the following strains of *Bacillus licheniformis*: ATCC 14580 (=NCIB 9375), NCIMB 6346 (=DSM 8785), NCTC 1024, NCTC 1025, NCTC 2120, NCTC 7589, NCTC 9932, ATCC 21424, NCIMB 10689, and ATCC 53757. A preferred subgroup includes *Bacillus licheniformis* ATCC 14580 (=NCIB 9375), and *Bacillus licheniformis* NCIMB 6346 (=DSM 8785).

Strains of *Bacillus*, such as strains of *Bacillus licheniformis*, are known in the art and available from, e.g., culture collections like ATTC mentioned above, or they can be isolated from nature. Preparations of live, or livable, *Bacillus* cells may be prepared as is known in the art. Examples of such cells are vegetative cells, and spores such as endospores. In one embodiment a fermentation extract of the *Bacillus* strain is used, for example in the form of a spray dried fermentation liquor.

The test of Example 1 is a PCR reaction, in this example conducted with DNA isolated from various strains of *Bacillus licheniformis*. In a particular embodiment of this test, the DNA used as template for the PCR reaction is chromosomal DNA which can be isolated by methods known in the art. The result of the Example 1 test is positive when a PCR fragment of the right size is obtained. In Example 1, the right size is indicated as 0.4 kb. In a particular embodiment, the right size is between 0.35 kb and 0.44 kb (=350 bp-440 bp). In alternative embodiments, the right size is 330-430 bp, 340-420 bp, 350-410 bp, 360-400 bp, 370-390 bp, or 385-395 bp. The size of the coding sequence (CDS) of SEQ ID NO:1 is approximately 380 bp (viz. 378 bp).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

EXAMPLE 1

*Bacillus* Strains with L12-Like Genes, as Identified by PCR

Genes similar to the gene encoding the L12 protein (SEQ ID NO:1) were identified in a number of other *Bacillus licheniformis* strains by PCR. DNA for use as a template for the PCR reaction was isolated from eleven different *Bacillus licheniformis* strains grown overnight at 37° C. on TY agar plates (for recipe, see Example 1 of WO-A-2006/099871). One inoculation tube with cells from each strain were suspended in 0.1 ml H2O and boiled for 10 min, centrifuged, and 5 microliter supernatant from each was used as DNA template in PCR reactions as described below.

The PCR reactions were run in "Pure Taq™ Ready-To_Go™ PCR Beads" from Amersham Biosciences: 5 microliter DNA template+2×1 microliter of primer Pep481 (SEQ ID NO:4) and Pep482 (SEQ ID NO:5)+18 microliter H2O.

PCR program: 1) 95° C. 3 min; 2) 95° C. 10 sec; 3) 65° C. 30 sec −1° C. pr. cycle; 4) 72° C. 1min; 5) Go To 2) 9 times; 6) 95° C. 10 sec; 7) 55° C. 30 sec; 8) 72° C. 1 min; 9) Go To 6) 19 times; 10) 72° C. 5 min; 11) 4° C. forever, which means that following step 10) the temperature is lowered to 4° C. Primers:

```
                                           (SEQ ID NO: 4)
    Pep481 AATTACGCGTGTTGGTGCGATAGTAGTAACG-3'

(SEQ ID NO: 5)
    Pep482 TTAAGAATTCGAATGAAAGAGGAGGAATG-3'
```

The resulting 0.4 kb PCR fragment from five positive strains (positive meaning giving DNA band of the right size) were purified and used in a DNA sequencing experiment, using once again as sequence primers the Pep481 (SEQ ID NO:4) and Pep482 (SEQ ID NO:5) primers.

Three of the five positive strains gave the same DNA sequence: *Bacillus licheniformis* ATCC 14580, *Bacillus licheniformis* NCIMB 6346 (=DSM 8785) and *Bacillus licheniformis* strain 712, resulting in the amino acid sequence of SEQ ID NO:2. In *Bacillus licheniformis* strain 470 DNA changes resulted in two amino acid changes (SEQ ID NO:7), however none in the mature peptide. In *Bacillus licheniformis* strain 009 DNA changes resulted in fifteen amino acid changes (SEQ ID NO:6), eight of which in the mature peptide. Furthermore, a consensus sequence (SEQ ID NO:8) was derived from SEQ ID NOs:2, 6, and 7.

Note that, in this experiment, the nucleotides encoding the seven C-terminal amino acids of SEQ ID NO:2 are included in the Pep481 primer (SEQ ID NO:4), and the seven C-terminal amino acid residues of SEQ ID NOs:6-7 may therefore not be correct. However the correctness of SEQ ID NOs:6-7 was later confirmed.

In addition, 44 other strains of *Bacillus licheniformis* were tested as described above. A positive PCR-response was found in 27 of these strains. Examples of additional publicly available strains of *Bacillus licheniformis* found to be L12-positive have the following deposit numbers: NCTC 1024, NCTC 1025, NCTC 2120, NCTC 7589, NCTC 9932, ATCC 21424, NCIMB 10689, ATCC 53757. NCTC is the National Collection of Type Cultures. ATCC is the American Type Culture Collection. NCIMB is the National Collection of Industrial, Marine and Food Bacteria.

---

The invention claimed is:

1. A method of treatment of coccidiosis in an animal, comprising administering to the animal an L12 protein, where the L12 protein is:
   (a) a polypeptide which has a degree of identity to the sequence of amino acids 1-85 of SEQ ID NO:2 of at least 80%; or
   (b) a fragment of the sequence of amino acids 1-85 of SEQ ID NO:2.

2. The method of claim 1, wherein the animal is a human.

3. The method of claim 1, wherein the L12 protein has a degree of identity to the sequence of amino acids 1-85 of SEQ ID NO:2 of at least 80%.

4. The method of claim 1, wherein the L12 protein has a degree of identity to the sequence of amino acids 1-85 of SEQ ID NO:2 of at least 85%.

5. The method of claim 1, wherein the L12 protein has a degree of identity to the sequence of amino acids 1-85 of SEQ ID NO:2 of at least 90%.

6. The method of claim 1, wherein the L12 protein has a degree of identity to the sequence of amino acids 1-85 of SEQ ID NO:2 of at least 95%.

7. The method of claim 1, wherein the L12 protein has a degree of identity to the sequence of amino acids 1-85 of SEQ ID NO:2 of at least 97%.

8. The method of claim 1, wherein the L12 protein is a fragment of the sequence of amino acids 1-85 of SEQ ID NO:2.

9. The method of claim 1, further comprising administering to the animal a polyunsaturated fatty acid (PUFA).

10. A method of treatment of coccidiosis in an animal, comprising administering to the animal a strain of *Bacillus*, which expresses an L12 protein, where the L12 protein is:
    (a) a polypeptide which has a degree of identity to the sequence of amino acids 1-85 of SEQ ID NO:2 of at least 80%; or
    (b) a fragment of the sequence of amino acids 1-85 of SEQ ID NO:2.

11. The method of claim 10, wherein the animal is a human.

12. The method of claim 10, wherein the L12 protein has a degree of identity to the sequence of amino acids 1-85 of SEQ ID NO:2 of at least 80%.

13. The method of claim 10, wherein the L12 protein has a degree of identity to the sequence of amino acids 1-85 of SEQ ID NO:2 of at least 85%.

14. The method of claim 10, wherein the L12 protein has a degree of identity to the sequence of amino acids 1-85 of SEQ ID NO:2 of at least 90%.

15. The method of claim 10, wherein the L12 protein has a degree of identity to the sequence of amino acids 1-85 of SEQ ID NO:2 of at least 95%.

16. The method of claim 10, wherein the L12 protein has a degree of identity to the sequence of amino acids 1-85 of SEQ ID NO:2 of at least 97%.

17. The method of claim 10, wherein the L12 protein is a fragment of the sequence of amino acids 1-85 of SEQ ID NO:2.

18. The method of claim 10, further comprising administering a polyunsaturated fatty acid (PUFA) to the animal.

\* \* \* \* \*